US006925146B2

(12) United States Patent
Brauss

(10) Patent No.: US 6,925,146 B2
(45) Date of Patent: Aug. 2, 2005

(54) X-RAY DIFFRACTION SYSTEM

(75) Inventor: Michael Brauss, Amhertsburg (CA)

(73) Assignee: Proto Manufacturing Ltd., Oldcastle ( * ) Notice: Subject to any disclaimer, the term of this patent is extended or adjusted under 35 U.S.C. 154(b) by 0 days.

(21) Appl. No.: 10/390,479

(22) Filed: Mar. 17, 2003

(65) Prior Publication Data

US 2004/0184580 A1 Sep. 23, 2004

(51) Int. Cl.$^7$ ............................................... G01N 23/20
(52) U.S. Cl. .......................................... 378/81; 378/71
(58) Field of Search .......................... 378/70–73, 79–81

(56) References Cited

U.S. PATENT DOCUMENTS 4,412,345 A * 10/1983 Workman et al. ............. 378/78

* cited by examiner

*Primary Examiner*—Craig E. Church
*Assistant Examiner*—Jurie Yun
(74) *Attorney, Agent, or Firm*—Fitch, Even, Tabin & Flannery

(57) ABSTRACT

An open beam x-ray diffraction system and method are provided including modular x-ray heads for being detachably connected to a base unit having a common drive assembly that shifts the heads in an arcuate path during an x-ray diffraction measurement operation. The heads can be tailored to different performance criteria depending on the needs of the measurement operation that is to take place. To this end, one of the heads can be a microhead that is adapted to take measurements from otherwise difficult to access surfaces, such as on the inside of tubular parts. Enhancements to the drive assembly for improved accuracy and speed are also disclosed.

17 Claims, 13 Drawing Sheets

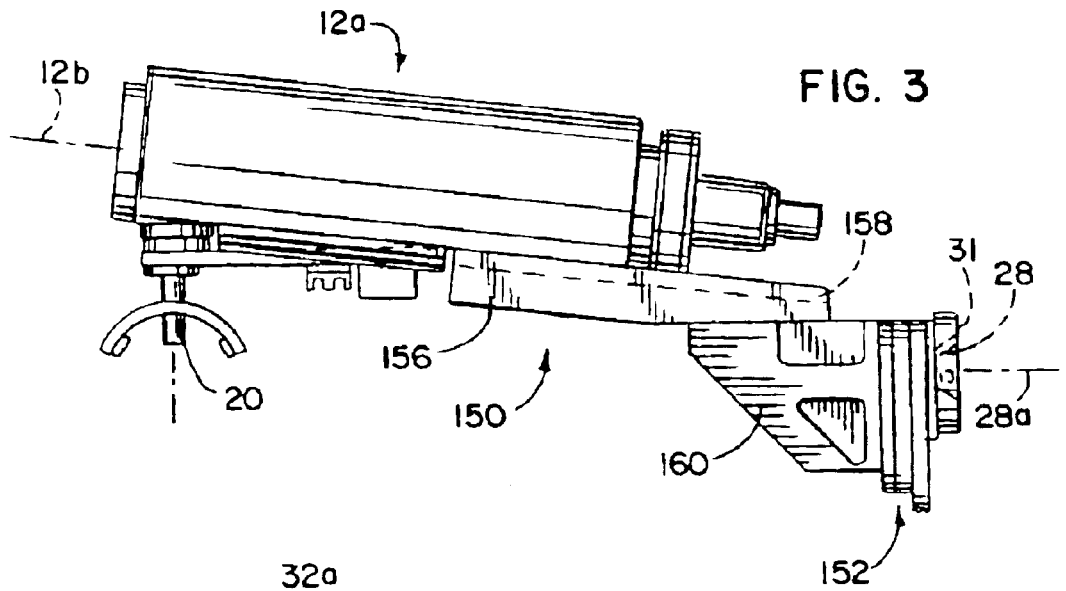
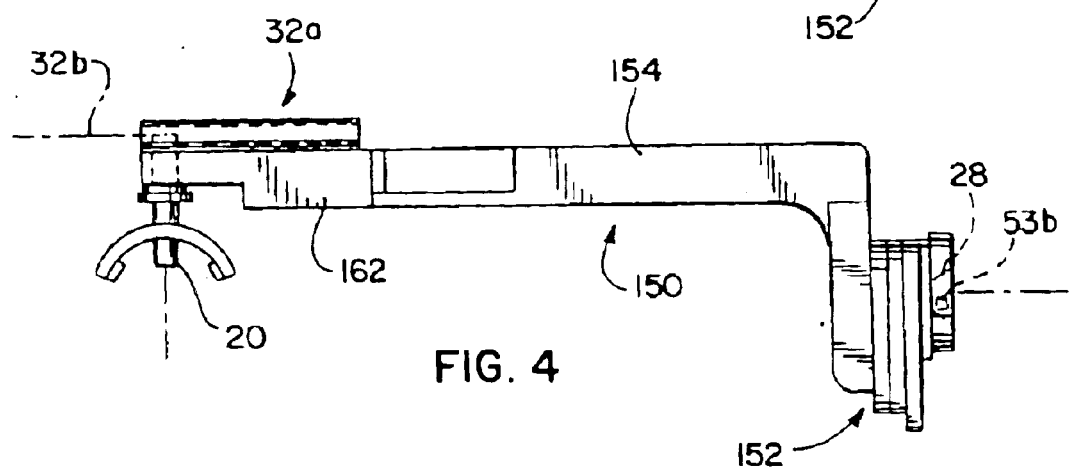
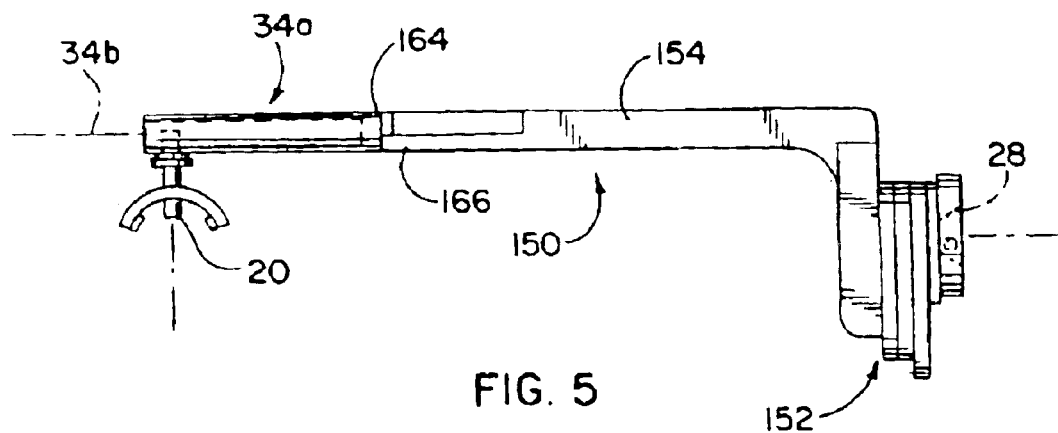

X-RAY DIFFRACTION SYSTEM

FIELD OF THE INVENTION

The invention relates to a system for measuring the strength-related characteristics of a part material using x-ray diffraction techniques and, more particularly, to a system that employs such techniques with parts of various sizes and configurations.

BACKGROUND OF THE INVENTION

The use of x-ray diffraction techniques for measuring residual stresses in crystalline substances such as metal or ceramic materials is well-known. The general idea with the use of x-ray diffraction is to subject the material to the radiation of x-rays with the resulting sensed x-ray diffraction peak interpreted to arrive at a measurement of a strength related characteristic, i.e. stress, retained austenite, hardness of the part material, to show, for instance, the level of fatigue in the material.

More particularly, the present invention relates to open beam type x-ray diffraction equipment that utilizes a cantilevered x-ray goniometer head having fiberoptic detectors carried toward the forward end of the head. In contrast, there are x-ray diffraction systems that are of a closed loop variety in the sense that the x-ray head is positioned at one location along a circular mount with the detectors spaced generally across from or diametrically opposite to the x-ray head along the circle mount with the part inserted in the space therebetween. In these systems, part size is limited due to this orientation of the x-ray head and detectors, and generally, coupons have to be taken from the part that is desired to be measured. With the open beam approach, coupons do not have to be cut out from parts since the x-ray head and detectors are integrated with each other. However, current open beam x-ray equipment still suffers from shortcoming as described below.

One such problem is that there is no open beam type x-ray apparatus that can perform these types of measurements on a wide variety of different parts and/or different materials or materials with different characteristics such as with respect to crystalline structure. Generally, the size of the goniometer or x-ray tube head relates to the power required for its operation. With greater power levels, the diameter of the x-ray tube is larger for heat dissipation purposes. The power for a goniometer head is selected to generate sufficient x-ray flux for the x-ray diffraction process to take place with particular materials or material characteristic.

The problem with the use of larger diameter x-ray heads for taking measurement is that with certain parts such as pipes and the like, it would be desirable for measurements to be taken of the material in the interior of the part. Depending upon the relative size of the inner diameter of the pipe and of the head on the x-ray diffraction apparatus, it may be physically impossible for the x-ray head to fit inside the pipe and take a suitable measurement. Also, where part surfaces are in confined areas such as in close confronting relation to each other as can be found on fillets of aircraft rotor disks at the roots of the rotor blades, set-up of the x-ray diffraction equipment to precisely direct the x-rays at the surface location from which a measurement is desired can be difficult, and is usually unwieldy where the large x-ray head itself has to be manipulated. Since current open-beam x-ray diffraction units have x-ray heads that are specifically tailored to a material or materials from which measurements are to be taken, many different sizes and types of x-ray diffraction units generally are necessary to take measurements on a wide range of different parts that are of different or materials or material characteristics, and/or having different configurations raising equipment costs accordingly. Thus, there is a need for an x-ray diffraction system and method that allow for greater flexibility in terms of the different types of parts and part geometries from which accurate x-ray diffraction measurements can be taken.

Another problem in using this equipment is the measurement precision that is desirable, and the issues this creates with the system's drive mechanism for pivoting or rotating the tube during a measurement operation. During x-ray measurement operations, the tube is typically pivoted to vary the position of the x-ray emitter or collimator from which x-rays are emitted toward the part to obtain more precise measurements by way of sampling techniques as opposed to keeping the tube and its collimator fixed relative to the part. As mentioned, the tube is generally cantilevered and is pivoted back and forth along a fixed arcuate rack by a motor drive including a pinion gear which pivots with the tube. In another configuration, the motor pivots the rack which is fixed to the tube. In both instances, the motor is also part of the cantilevered structure of the current x-ray diffraction units. Thus, current x-ray diffraction units have heavy cantilevered weights, particularly those having larger x-ray tubes. Since the x-ray diffraction techniques employed rely on distinguishing minute differences in the diffraction peaks and patterns of the detected x-rays, precision is required for pivoting the x-ray head. Inaccuracies can be created in present drive mechanisms with transmission belts that stretch and/or with backlash problems that occur between meshed gears due to play therebetween such as with the above-described rack and pinion arrangement. Therefore, there exists a need for a drive mechanism that provides for precision movements of the x-ray head for taking efficient and accurate measurements therewith.

Various part sizes and configurations pose yet another problem for standard x-ray diffraction measurement techniques in that the preferred measurement technique, d v. $Sine^2 \psi$, cannot be used to measure all part configurations. When using this technique, the sensors are positioned such that they remain in a plane that is parallel to the plane of angular rotation of the head itself. This technique is the most accurate way to measure strength related characteristics of parts because of the geometrical relationship between the x-ray emitter, part, and sensors. However, this technique requires enough room to allow the head to oscillate back and forth without having the sensors hit the part itself. Therefore, there are situations where a different method of measuring, called d v. $Sine^2 \chi$, must be used. When using this technique, the sensors are in a position that is shifted by ninety degrees about the longitudinal axis of the emitter from the d v. $Sine^2 \psi$ configuration so that the sensors are generally aligned or parallel to the longitudinal axis of the x-ray tube. Then the head rotates as it normally does during x-ray diffraction measurements. This sensor configuration allows the user to take measurements in narrow places such as between the roots of blades. However, utilizing the d v. $Sine^2 \chi$ technique requires a sacrifice in measurement accuracy. Currently, one has to switch x-ray diffraction apparati in order to change from one technique to another. Accordingly, an x-ray diffraction apparatus that has flexibility in terms of the measurement techniques it employs would be desirable.

SUMMARY OF THE INVENTION

In accordance with one aspect of the present invention, an x-ray diffraction apparatus is provided having x-ray or goniometer heads that are modular to allow them to be switched with one another to optimize the performance of the apparatus. In this manner, measurements can be taken from a wider spectrum of part sizes and configurations and of different part materials or material characteristics without requiring different x-ray diffraction unit by using the same base x-ray diffraction apparatus in conjunction with different modular heads that are selected according to the operating requirements for the part from which measurements are to be taken. For instance, if the part includes measurement sites that are difficult or impossible to access with standard larger size x-ray tubes such as pipe interior surfaces, a smaller x-ray head can be exchanged with a larger head and removably attached to the apparatus for taking x-ray diffraction measurements therewith. If a high power x-ray head is preferable due to part materials and/or geometry, then a larger x-ray head can be exchanged onto the apparatus for the smaller head. As is apparent, rather than having a different x-ray diffraction unit for each different head with the floor space and expense this entails, the present invention allows for a single base unit to be employed with different modular x-ray heads to allow them to be switched with one another to optimize the performance of the apparatus. Programmable modules can be associated with each head to transmit information to the base unit controller relating to the size and other operational and performance characteristics of the specific head including its x-ray detector system connected to the unit for proper operation thereof without the need to enter such information each time a head is exchanged.

The modular heads each have an x-ray tube, and emitter/sensor assembly, and an adapter portion for connecting the head to the base of the apparatus, and more particularly a cooperating adapter portion thereof. The head adapter portion may be a socket that connects to the base adapter portion in the form of a shaft of the base, the shaft being driven by a drive train and motor to shift the x-ray head as described further herein. In the preferred form, the socket is conical, and the shaft has a conical terminus for mating in the x-ray head socket. To positively fix the shaft in the socket opening, the shaft can include a keyway and the head adaptor may have a key which mates and releasably locks into the keyway to prevent relative rotation between the shaft and x-ray head detachably connected thereto. Alternatively, the key and keyway can be reversed with the shaft being keyed and the socket including a keyway.

Each x-ray tube head has an emitter or collimator which depends from the tube generally perpendicular to the tube longitudinal axis for directing x-rays down toward the part. An arc mount is provided for detectors at either end thereof, and the emitter collimator bisects the arc mount, as is the typical configurations for these emitter/sensor assemblies on current x-ray tubes. Accordingly, operation of the motor or the base unit rotates the output shaft adapter which, in turn, rotates the x-ray tube detachably connected to the unit shaft adapter via the socket adapter portion thereof. Thus, rotation of the head adapter portion and the tube attached thereto causes the collimator carried toward the forward end of the tube to shift along a predetermined arcuate path so that x-rays are directed at a region on the part from different angles of attack from the x-ray tube head. Although the x-ray head assembly is cantilevered forward from the base unit, the drive mechanism including the motor and drive transmission including the output shaft are all disposed in the base unit to minimize the cantilevered weight of the modular x-ray heads thus improving the accuracy of the movements thereof in contrast to the heavier prior x-ray heads that had their pivot drive mechanisms integrated at the head to be cantilevered as previously described.

In another aspect of the invention, an improved drive assembly is provided which includes an anti-backlash mechanism to provide precision shifting for the head upon operation of the drive motor. Such precision shifting enables more accurate x-ray diffraction measurements to be taken. The anti-backlash mechanism preferably employs a split gear that is associated with the drive train, and more specifically the adapter shaft assembly of the base drive unit. The gear is split axially into gear portions that have their corresponding teeth portions oppositely biased relative to each other. In this manner, the faces of the teeth of the split gear stay firmly engaged against the faces on the teeth of the motor drive shaft gear so as to substantially minimize any loose spaces or play therebetween. Alternatively, the split gear could be provided on the motor drive shaft for meshing with a gear on the output shaft assembly.

Unlike prior rack and pinion drive systems as previously described, the split gear avoids backlash that can occur in the prior drive systems when the motor changes direction when the x-ray head has reached the end of its travel along the rack at one end or the other thereof. The rack and pinion system causes inaccuracies to be introduced into the measurements that are taken by the x-ray head due to the play between the gears as the motor changes directions. In contrast, the present split gear keeps its teeth firmly engaged against the teeth faces of the motor gear even when the motor is changing directions toward the end of the arcuate travel path in one direction or the other. Accordingly, the present anti-backlash mechanism avoids the inaccuracies caused by the play between the gear teeth in the prior drive systems.

As previously mentioned, the modularity of the x-ray heads of the present x-ray diffraction apparatus enables x-ray heads of varying sizes and/or configurations to be employed on the same base unit. To this end, the heads can include sizes ranging from relatively large heads of, for example, approximately four inches in diameter, to extremely small or micro-heads which can be on the order of approximately one and one quarter inches down to three-eighths of an inch in diameter. The window in the tube aligned with the collimator that allows passage of the x-rays generated in the tube to the collimator is normally brazed to the tube material, e.g. stainless steel. However, the problem with utilizing an intermediate brazing material in the microtube is that it increases the chances for melting which increases the potential for contaminating the tube and generating leakage from the tube. Accordingly, the preferred window utilized with the microtube x-ray head is electron-beam welded to the tube material to avoid intermediate brazing material.

Another adaptation for the microtube is the use of a flexible circuit board that receives signals from the detectors for processing thereof. The flexible circuit board can conform to the curved surface of the microtube x-ray head so as to avoid significantly increasing the diameter thereof. Generally, with prior larger x-ray tubes, the detectors are connected by fiber-optic cabling to a processor unit mounted toward the back of the x-ray head or thereabove thus creating impediments for maneuvering the head such as may be required for difficult part geometries. Accordingly, the use of the flexible circuit boards on the microtube maintains its enhanced flexibility in reaching hard-to-access target surfaces on parts from which x-ray diffraction measurements are to be taken.

In the other larger heads in the modular x-ray head set that can be employed with the present modular x-ray diffraction apparatus, another advantageous feature that can be implemented is the ability to shift the emitter/sensor assembly relative to the x-ray head so that both principle mathematical techniques, d v. $Sine^2\psi$ and d v. $Sine^2\chi$ are available to be utilized. While the modularity of the x-ray heads provided in the preferred system herein allows for the different emitter/sensor configurations to be fixed on different tubes that can be easily changed out depending on which measuring technique is to be utilized, the shifting of the emitter/sensor assembly on a particular tube is preferable from a convenience standpoint to avoid having to exchange tubes as has been described.

Typically, the emitter/sensor sub-assembly includes an arc to which the sensors are mounted as previously described. With the sensors in the d v. $Sine^2\psi$ orientation, they are offset on either side of the tube longitudinal axis, and thus can serve as impediments to tube maneuverability when measuring difficult part geometries.

Accordingly, by allowing for the shifting of the sensor arc so that it is in the d v. $Sine^2\chi$ orientation with the sensors aligned along the tube axis, the x-ray head can be better positioned as the arc is now in a minimally invasive orientation thereof, albeit invoking the mathematical technique that is less precise for x-ray diffraction purposes.

In one form, a manual actuator is provided which allows an operator to manually adjust the position of the sensors between the above-described configurations. The manual actuator can be a pin that is biased into a selected one of two apertures corresponding to the configuration for the sensors that is desired. The pin includes a handle pull ring to allow a user to pull it out from the aperture against its bias for shifting of the sensors to the other configuration. With the pin aligned with the other aperture, the pull ring is released and the pin is biased into the aligned aperture to fix the sensors in the selected configuration. Accordingly, the pull ring manual actuator allows for very efficient and quick adjustments to be made to the sensor configuration to allow the larger x-ray heads to be more flexibly employed with a variety of different part configurations.

BRIEF DESCRIPTION OF THE DRAWINGS

FIGS. 3–5 are elevational views of different sized modular x-ray heads each including identical rear socket adaptor portions for mating with the output shaft adaptor portion of the drive unit;

DETAILED DESCRIPTION OF THE PREFERRED EMBODIMENTS

Figure 1:
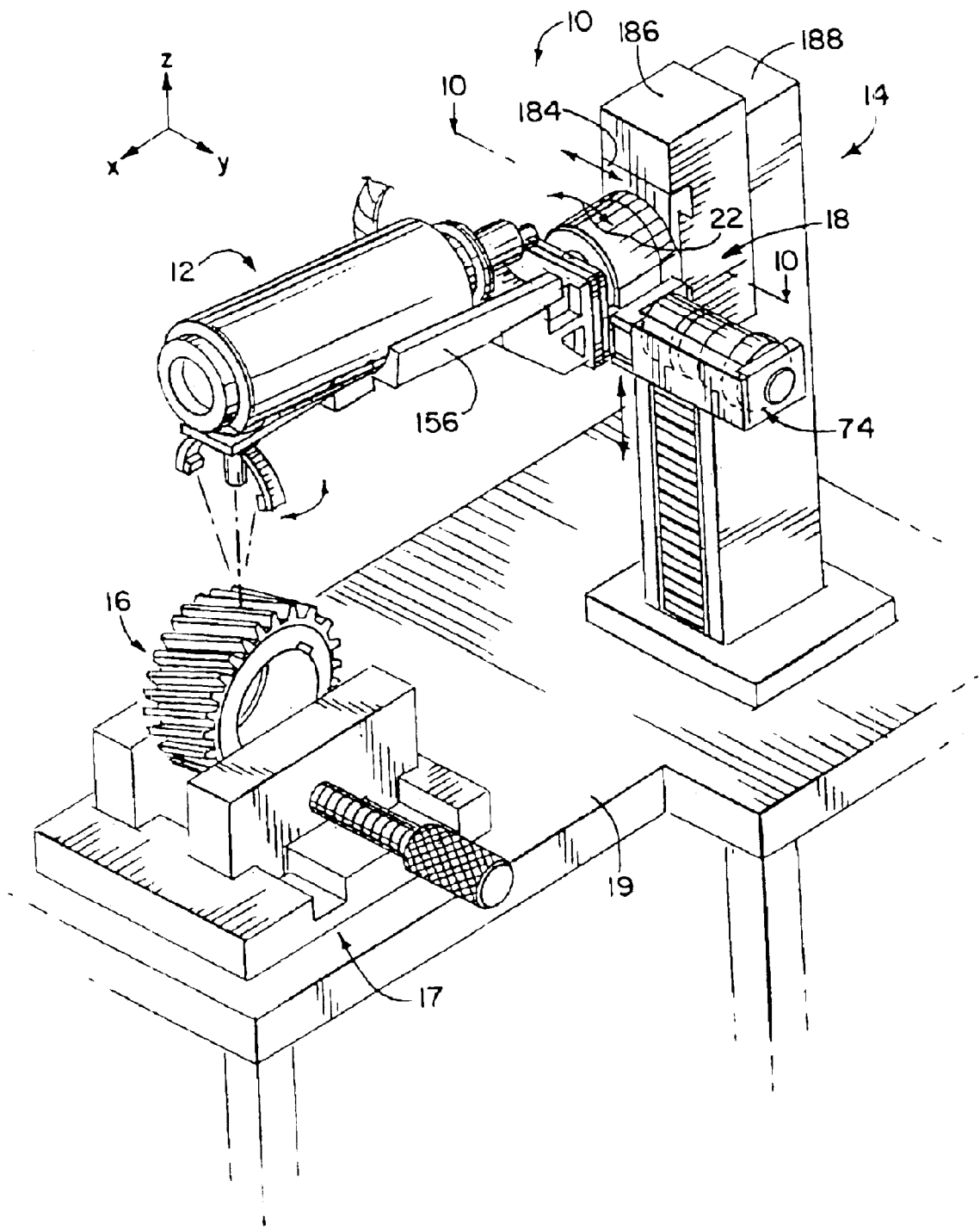
FIG. 1 is a perspective view of an x-ray diffraction system in accordance with the present invention showing an x-ray head having a collimator and sensors for taking x-ray diffraction measurements from a part fixed therebelow.

Referring initially to FIG. 1, an x-ray diffraction apparatus 10 in accordance with the present invention is depicted in a representative embodiment and set-up with the apparatus 10 including a modular x-ray goniometer head 12 that is detachably connected to base unit 14 for taking x-ray diffraction measurements from various parts such as the illustrated gear 16 rigidly held by fixturing 17 therebelow. The x-ray head can be shifted in a plurality of different linear directions such as in the vertical Z-axis direction as well as in the lateral Y-axis direction, as shown. X-axis fore and aft direction shifting can also be provided as well as rotary or pivot shifting of the head 12 about different pivot axes. A common drive assembly 18 (FIG. 10–12) shifts the x-ray tube head assembly 12, and particularly the emitter or collimator 20 depending from the tube housing 12a at the forward end portion thereof in arcuate path 22 so that as the tube oscillates back and forth in its arcuate path 22, x-rays are directed at the region on the part 16 from a variety of different angles to provide several different data points from which measurement information can be gleaned. Frame 19 of the base unit 14 can support both the part 16 along with its fixturing 17 and the drive assembly 18.

Figure 2:
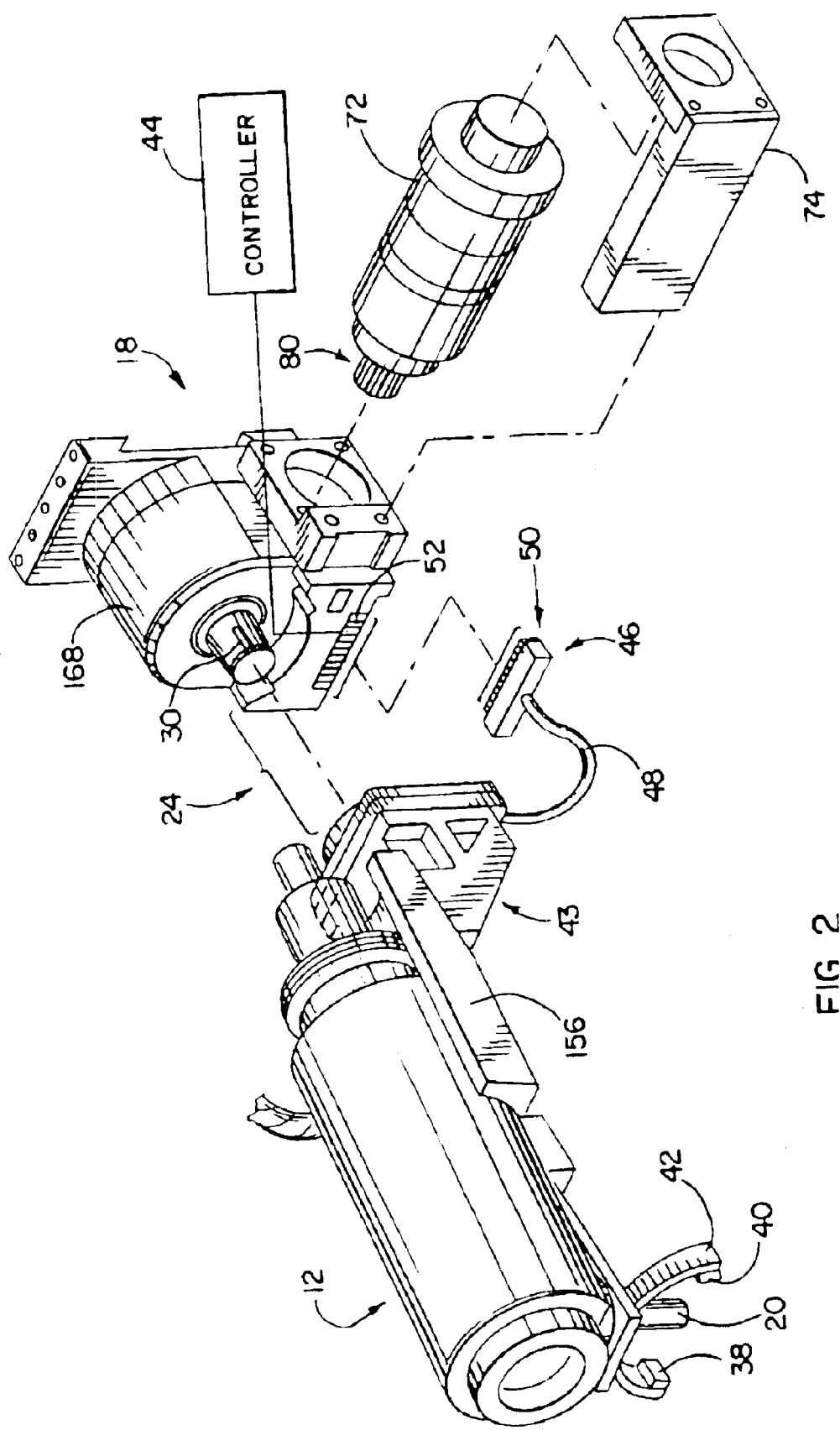
FIG. 2 is an exploded perspective view of the x-ray diffraction unit shown in FIG. 1 showing an adaptor between the motor base unit and the modular x-ray head including an output adapter shaft portion of the motor unit.

To allow different x-ray generator tube heads or head assemblies (see FIGS. 3–5 and 28) to be interchanged onto the base unit 14 to be driven by the common drive assembly 18, an adapter, generally designated 24, is provided between each of the heads and the base unit 14, as shown in FIG. 2 with respect to head 12. In the preferred and illustrated form, the adapter 24 includes an output shaft end portion 26 associated with the base unit 18 and a socket portion 28 associated with each of the x-ray heads. Manifestly, the adapter portions 26 and 28 can be reversed on the heads and base unit, although it is preferred to have the shaft portion 26 on the mount 14 so that the set of modular x-ray heads do not have the small projecting part for its adapter portion 28.

The output shaft adaptor portion 26 and the socket adaptor portion 28 may be provided with a conical or frustoconical configuration so that they mate together with the conical surfaces in close fitting relation with each other to provide ease in alignment in making the connection for the adapter 24 herein. Rotation of the output shaft adaptor portion 26 is generated by operation of the drive assembly 18 for shifting the tube head 12 in its arcuate path 22. For this purpose, a key and keyway connection can be provided in the adapter 24 as by an axially extending key projection 30 formed on the adapter shaft 26 that can fit into an axial recess 31 formed in the socket 28 when angularly aligned therewith. In this manner, the output shaft adaptor portion 26 is non-rotatably received in the socket 28 for transmitting torque from the drive assembly 18 to the tube head 12 so that it is oscillated in its arcuate path 22 with motor operation.

The provision of modular x-ray generator head assemblies allows the different heads to be tailored for different part and material requirements for taking x-ray diffraction measurements therefrom. It is currently envisioned that the x-ray heads can be provided in different sizes and configurations such as shown in FIGS. 3–5 and FIG. 28 with there being a large x-ray head 12 (FIG. 3), an intermediate size x-ray head 32 (FIG. 4), and a microhead 34 (FIG. 5). Also, a specially dedicated x-ray head 200 (FIG. 28) can be provided that allows for x-ray diffraction measurements to be taken from a very particular part geometry, as discussed more fully hereinafter. Accordingly, the present apparatus 10 allows a single base unit 14 to be employed with several different x-ray heads such as the illustrated set of heads 12, 32, 34 and 200. In this example, the x-ray head 12 can be employed where higher power requirements are required for generating x-rays to take measurements from a particular part material, whereas the smaller heads 32 and 34 can be used where the power is not as critical and access to difficult part geometries is needed. In particular, with the microtube 34, it can be maneuvered into confined spaces such as found inside on the interior of tubular parts for taking x-ray measurements from the interior surfaces thereof. Head assembly 200 is specially adapted for taking measurements from small through bores that are of a relatively shallow depth such as the illustrated bolt holes 202 found in aircraft rotor discs 204.

Beyond size, the modular heads can be tailored in several other respects as well. For example, the wavelength generated for the x-rays can be tailored to the material to be measured so as to better match the lattice structure thereof. To do this, the material for the target anode 36 at the forward high voltage end in each of the tube heads can be varied. Exemplary anode materials can include copper, cobalt, wolfram, silver, molybdenum, manganese, iron and titanium. The beam shape can be tailored to the piece to be measured as by providing different collimators 20 on the various x-ray heads. For example, for those pieces that have surfaces in long narrow crevices or holes that are desired to be measured, the collimator 20 can be configured to generate a narrower x-ray beam to avoid measurement errors.

In addition to the collimator, an x-ray detector assembly 37 is provided as carried by each of the x-ray heads including x-ray detectors or sensors 38 and 40 that are typically mounted on either side of the collimator 20 via an arcuate x-ray mount 42. The x-ray heads can have the position of these detectors 38 relative to the collimator 20 varied along the mount 42 or on differently sized mounts 42 from one head to the other so that they are matched with the x-ray wavelength generated by the head and the response of the material for which the x-ray head is to be used for taking x-ray diffraction measurements from. The mount 42 itself can be shifted to provide for different measurement techniques or to accommodate different diffraction angles such as in assembly head 200, as will be discussed hereinafter. As is apparent, the provision of modular x-ray heads such as x-ray heads 12, 32, 34 and 200 enables much greater flexibility in tailoring the apparatus 10 to the particular needs of the x-ray diffraction operation that is to take place without necessitating several different x-ray diffraction units for this purpose.

Figure 20:
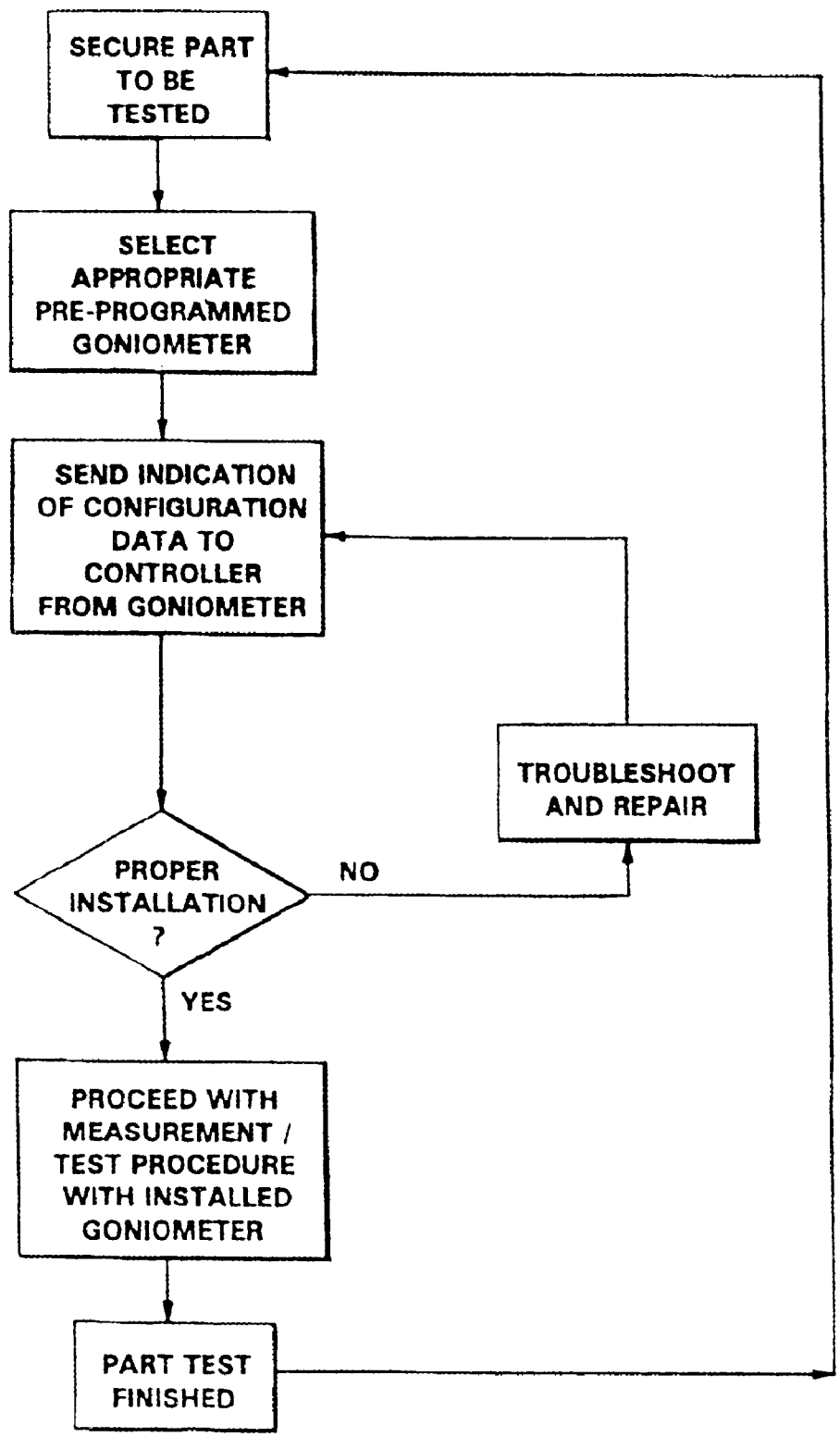
FIG. 20 is a flow diagram showing the steps for taking x-ray diffraction measurements with the present modular x-ray head apparatus.

Another feature of the preferred modular x-ray head apparatus 10 is the use of an electronic control system that includes a programmable module 43 associated with each of the x-ray heads 12, 32, 34 and 200, a controller 44 associated with the base unit 14, and an electrical link 46 that can interconnect the module 42 to the controller 44 with a selected one of the heads detachably connected to the unit 14. As can be seen in FIG. 2, the electronic link 46 can include a cable 48 connected to the module 43 and having a pin connector 50 at its free end which is adapted to be plugged into a socket connector 52 secured to the base unit 14. In one aspect, data flow to the controller 44 is not enabled unless the head is properly connected to the base unit via the adapter 24. To this end, electrical contacts 53a and 53b can be provided disposed on the adapter portions 26 and 28, respectively to be in electrical communication when the portions are properly mated together. In this manner, the contacts also form part of the electrical connection 46 for the control system. If the installation is completed successfully with the contacts 53a and 53b in electrical communication, when the pin connector 50 is plugged into the socket connector 52, the controller 44 recognizes that proper installation has occurred and autoconfigures the system to allow the measurement operation to properly proceed for the selected head, as depicted in the flow chart of FIG. 20.

The module 43 can include programmable memory so that it can be preprogrammed with information relating to the particular x-ray head with which it is carried. For example, the x-ray heads can be specifically tailored to measure a specific type of material or material characteristic as by generating an appropriate amount of x-ray flux and x-rays in the wavelength necessary for obtaining diffraction measurements from the part to be measured therewith. Thus, when x-ray head installation is successful, the controller 44 will have information or system configuration data transmitted thereto such as relating to the particular x-ray head that is attached to the base unit 14 such as the size of its collimator 20, the material type of its anode 36, as well as the size of the x-ray tube head itself and its power rating. For example, with the three different sizes of x-ray heads 12, 32 and 34 discussed herein, each can have different power ratings correlated to their size. Accordingly, the large x-ray head 12 may have a diameter of approximately four inches and a power rating of 3000 watts, the intermediate x-ray head 32 may have a diameter of approximately 1½" and a power rating of 300 watts, and the micro x-ray head 34 may have a diameter of approximately one and one quarter inches down to approximately three-eighths of one inch and a power rating of 200 watts or less. In addition, the power requirements for a particular size of tube head can be varied such as when there are heads of the same size that have different target anodes 36 from each other. In each instance, the control system will be provided the power rating of the particular modular x-ray head that is connected to the base unit 14 via the electrical connection 46 provided between the programmable module 42 and the controller 44. Once such information is received, the controller 44 regulates power supply to enable operation of the x-ray head in accordance with the power rating thereof.

Other variables between the x-ray heads which can be transmitted as data information to the controller 44 include the focal distance of the x-ray head and the details of the x-ray detector system 37 such as detector type or number of detectors, detector width and resolution provided by the detectors. Also, if the x-ray head employs a detector configuration that is fixed, the module 42 associated therewith can be programmed to indicate the measurement technique to be employed by the control system as dictated by the predetermined fixed detector configuration.

Figure 6:
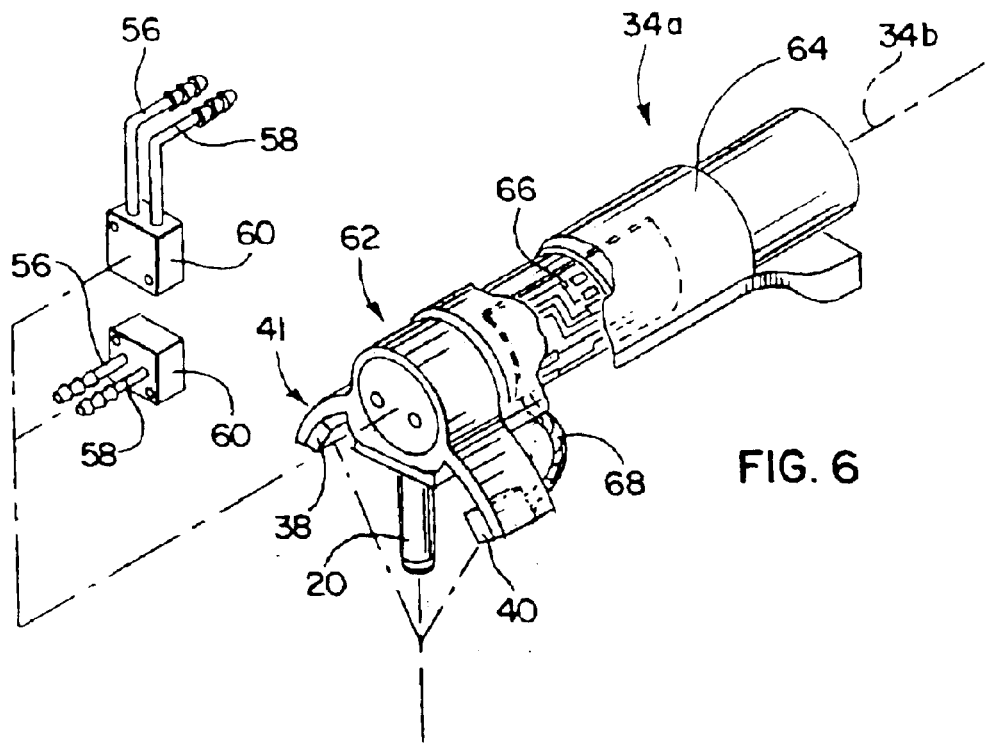
FIG. 6 is a perspective view of the micro-x-ray head of FIG. 5 showing a fixed sensor arrangement thereof and a flexible circuit board for processing signals from the sensors.
Figure 7:
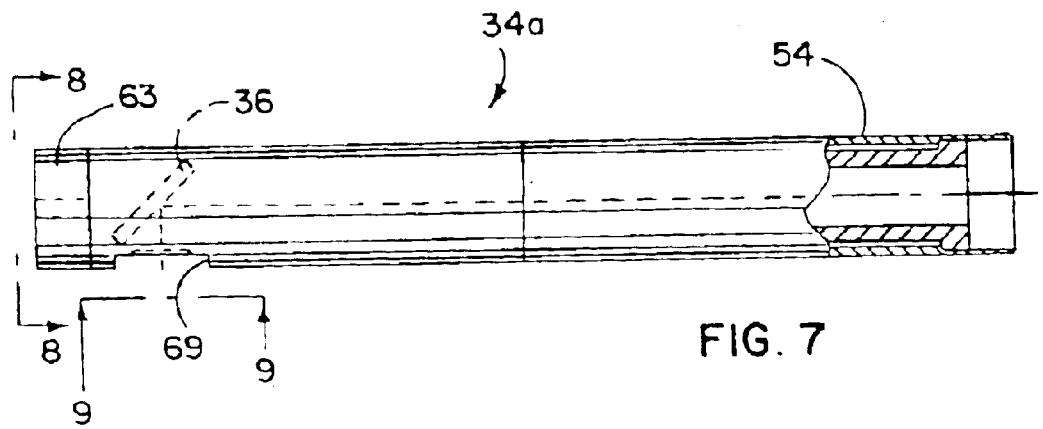
FIG. 7 is a side-elevational view partially in section of the x-ray head of FIG. 6 showing the construction of the tube walls thereof and a target anode in ghost.
Figure 8:
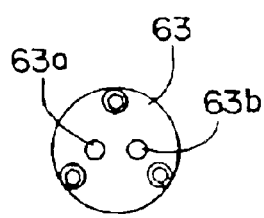
FIG. 8 is a front elevational view taken along line 8—8 of FIG. 7 showing front inlet and outlet cooling ports for the tube.

The small or micro tube x-ray head 34 disclosed herein can include alternative cooling systems provided therefor. Referring to FIG. 6, the typical cooling system for known x-ray heads employs cooling lines 56 and 58 that feed and remove cooling fluid, such as water or a glycol based fluid, to the tubular housing 54 via a fluid manifold 60 mounted to the forward or free end 62 of the head as by cap member 63 connected thereto. As shown with respect to microhead 34, the cooling lines 56 and 58 extend upwardly and then are run back toward the unit 14 along the top of the housing 54. Such a configuration effectively increases the size or diameter of the tube housing 54 in terms of its ability to be advanced into confined spaces such as found on the inside diameter of tubular parts. Accordingly, an alternative cooling system is also depicted for the microhead 34 wherein the cooling lines 56 and 58, rather than extending back along the exterior of the tubular housing 54, continue forwardly from the x-ray head 34 through cooling line ports 63a and 63b formed in the housing cap 63. In this manner, the cooling lines 56 and 58 do not increase the effective diameter of the tubular housing 54 allowing it to be advanced into the interior of tubular parts that may have only a slightly larger inner diameter than the diameter of the microtube housing 54 without encountering interference from the cooling lines 56 and 58 such as when they are run along the outer surface thereof.

Another adaptation for the microtube 34 in particular resides in the use of a flexible circuit board 64 including a circuit 66 printed thereon that processes signals received from the detectors 38 and 40 on either side of the collimator 20. In prior x-ray heads, the detectors include cabling that extend therefrom generally upwardly to a control unit for processing x-ray signals which restricts the maneuverability of these heads and their ability to access confined spaces. On the other hand, with the flexible printed circuit board 64 herein, only a very short length of fiberoptic cable 68 extending between the detectors 38 and 40 and the circuit board 64 need be provided as the board 64 can be secured to the outer surface of the tubular housing 54 toward the end 62 thereof in close proximity to the detectors 38 and 40 and in substantial conformance therewith wrapped about the housing 54. In this manner, the effective diameter of the tubular housing 54 is only nominally increased as by the thickness of the thin printed circuit board 64 with the attendant advantage of removing the impediments caused by having large and long lengths of cabling extending up from the detectors 38 and 40 to a fixed processing unit above the x-ray head as in prior systems. Accordingly, with the present flexible circuit board 64 including circuit 66 adapted for processing the x-ray detector signals, the length of the detector cables is minimized as it extends only for the distance between the detectors 38 and 40 mounted to the integrated arc mount 41 at either end thereof to the outer surface of the tubular housing 54 to which the circuit board 64 is secured. As can be seen in FIG. 6, the circuit board 64 is formed of material that is of sufficient flexibility to allow it to be bent and curved around the outer curved surface of the housing 54 so that it is in flush engagement therewith when secured thereto.

Figure 9:
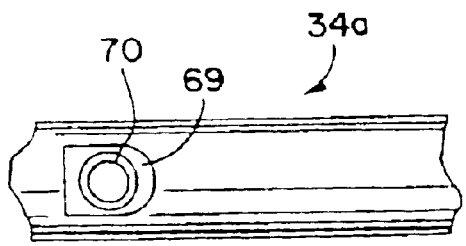
FIG. 9 is a bottom plan view taken along line 9—9 of FIG. 7 showing the window formed at the bottom of the tube for directing x-rays therethrough.

As shown in FIG. 9, the micro tube head 34 includes a bottom recess 69 toward the forward end 62 and having a window 70 aligned with the collimator 20 which allows the passage of x-rays as generated in the tube 34a and directed therethrough via the target anode 36 but keeps a vacuum intact in the housing 54. Generally, these windows are brazed to the material of the tubular housing via an intermediate brazing material. However, the small volume inside the microtube housing 54 along with the high vacuum required therein creates problems with the use of brazing material such as due to melting thereof which can contaminate the interior of the housing 54 as well as allow for undesired x-ray flux leakage therefrom. Accordingly, the preferred microtube housing 54 employs a window such as of a beryllium material joined to the stainless steel material of the tubular housing 54 by electron beam welding so that an intermediate brazing material is not used. In this regard, the present miniature x-ray tube head 34 including the electron beam welded window 70 does not have brazing material present and thus avoids the contamination and leakage problems found with brazed windows as is used in prior x-ray heads.

Figure 28:
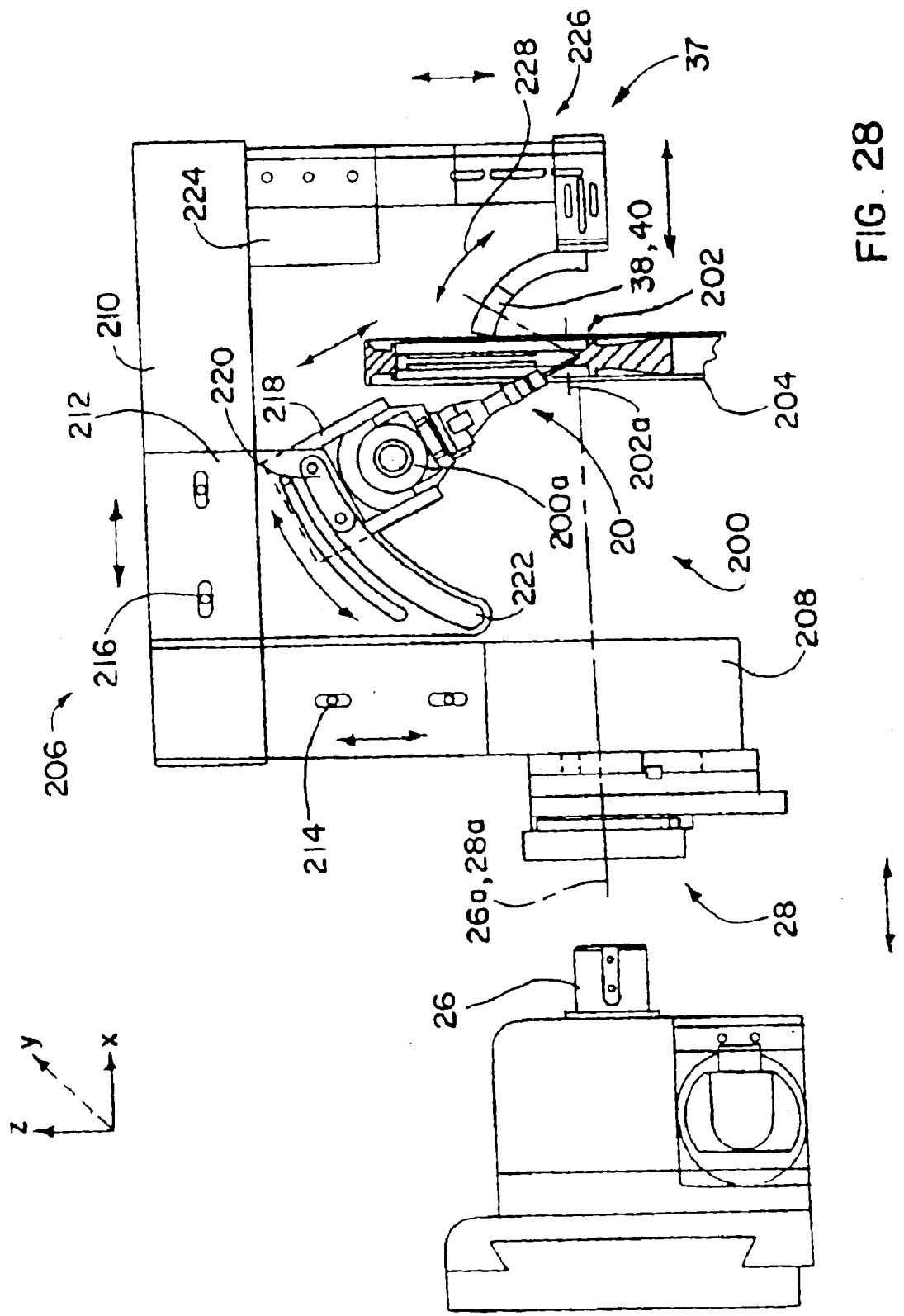
FIG. 28 is a side elevation view of another modular x-ray head assembly for taking x-ray diffraction measurements from surfaces in small and shallow through openings.
Figure 29:
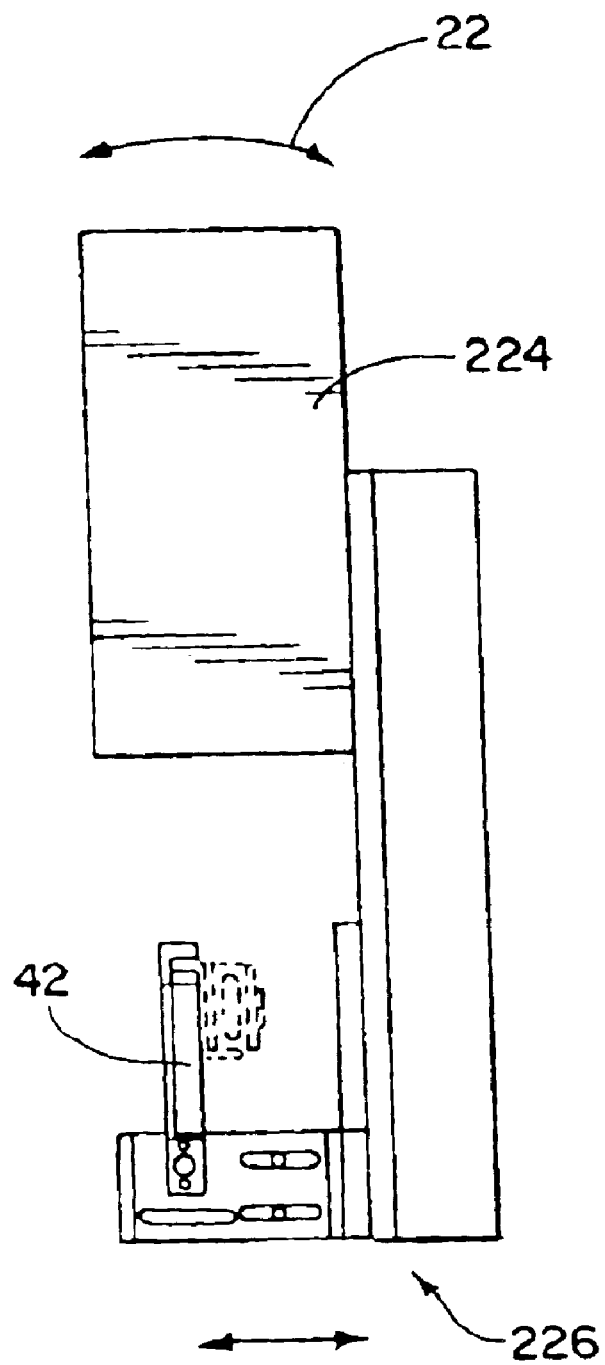
FIG. 29 is a front elevational view of the x-ray head assembly of FIG. 28 showing a lateral adjustment mount for the x-ray detectors.

Referring next to FIGS. 28 and 29, the illustrated head assembly 200 shown is especially well suited for taking x-ray diffraction measurements from the interior surfaces of throughbores such as the illustrated fastener through bore 202 in aircraft disc 204. The x-ray tube 200a can be oriented in a different configuration from the previously described tubes 12a, 32a, and 34a via a carrier support 206 therefor. In this regard, the x-ray tube 200a can extend laterally in the y direction transverse and, more specifically, perpendicular to the orientation of the previously described x-ray tubes 12a, 32a and 34a.

The carrier support 206 can have a generally U-shaped configuration opening downwardly toward the part 204 from which x-ray diffraction measurements are to be taken with the x-ray tube 200a provided with an overhead support generally above and off to one side of the part. More specifically, the support 206 includes a rear, vertically extending portion 208 which includes the socket adapter portion 28 toward the bottom thereof. Toward the upper end of the vertical portion 208, there is a forwardly extending portion 210 including a hanger 212 that supports the x-ray tube 200a forwardly of the rear support portion 200a and below the upper portion 210.

Frame portions 208 and 210 and hanger 212 include an adjustable mounting therebetween as by adjustment slots 214 and associated guide fasteners that allow the tube head 200a to be vertically adjusted in the z-axis direction and adjusted in the fore and aft x-axis direction. In addition, head assembly 207 includes an upwardly extending flange 218 that has followers 220 for being adjustably secured in an arcuate guide slot 222 of the hanger 212 to provide for arcuate adjustments of the head 207 in a compound x and z axis angular direction. By way of the adjustability provided by the carrier support 206, the position of the collimator 20 can be adjusted to allow for the angle of attack of the x-ray beam emitted therefrom to be varied relative to the part 204, and specifically the throughbore 202 having its axis 202a extending in the x-axis direction. In this manner, the optimum orientation of the tube 200a and collimator 20 thereof can be achieved relative to the configuration and size of the through bore 202.

Similarly, the detector assembly 37 can be adjustably supported by the carrier support 206, and specifically via a forward, downward extension 224 thereof. As shown, the extension 224 projects downwardly from the front end of the upper support portion 210 with the detector assembly 37 including the arc mount 42 thereof being adjustably secured to slotted slide bracketing 226 to position the detectors on the side of the part 204 opposite to the side at which the tube 200a and collimator 20 are disposed. The slide bracketing 226 can allow for x, y and z adjustments of the detector assembly 37, as can be seen in FIGS. 28 and 29. In this manner, the detectors 38 and 40 secured to the arc mount 42 can have their position optimized for detecting x-rays defracted from the inner surface of the throughbore 202. In addition, the slide bracketing 226 can allow for the mount to be angularly adjusted in path 228, as shown in FIG. 28.

As previously mentioned, the drive assembly 18 for oscillating the x-ray heads in their arcuate path 22 during an x-ray diffraction measurement operation is integrated into the base unit 14 rather than being integrated with the x-ray head assembly and cantilevered forwardly along with the heads from the base unit 14 as in prior x-ray diffraction systems. In this manner, the weight of the drive 18 does not affect the x-ray diffraction measurement operation either in terms of its speed or its accuracy unlike prior systems. As shown, the present x-ray head drive assembly 18 includes a motor 72 that is mounted to the base unit 14 as by bracket 74. The motor 72 includes a drive shaft 76 which transmits rotary power to the output shaft assembly 77 including end adaptor portion 26 thereof. In the illustrated and preferred form, the drive assembly 18 includes worm gear transmission drive 78, as shown best in FIG. 12. The drive shaft 76 extends transverse and in particular, perpendicular to the output shaft assembly 77, and the worm gear drive 78 includes driver gear 80 on the drive shaft 76 and driven gear 82 on the output shaft assembly 77. In the preferred worm gear drive 78 herein, the driver gear may be a worm driver gear 80, and the driven gear may be a worm wheel 82 with each of these gears 80 and 82 including respective helical gear teeth 80a and 82a for being meshed in driving relation with each other.

Figure 12:
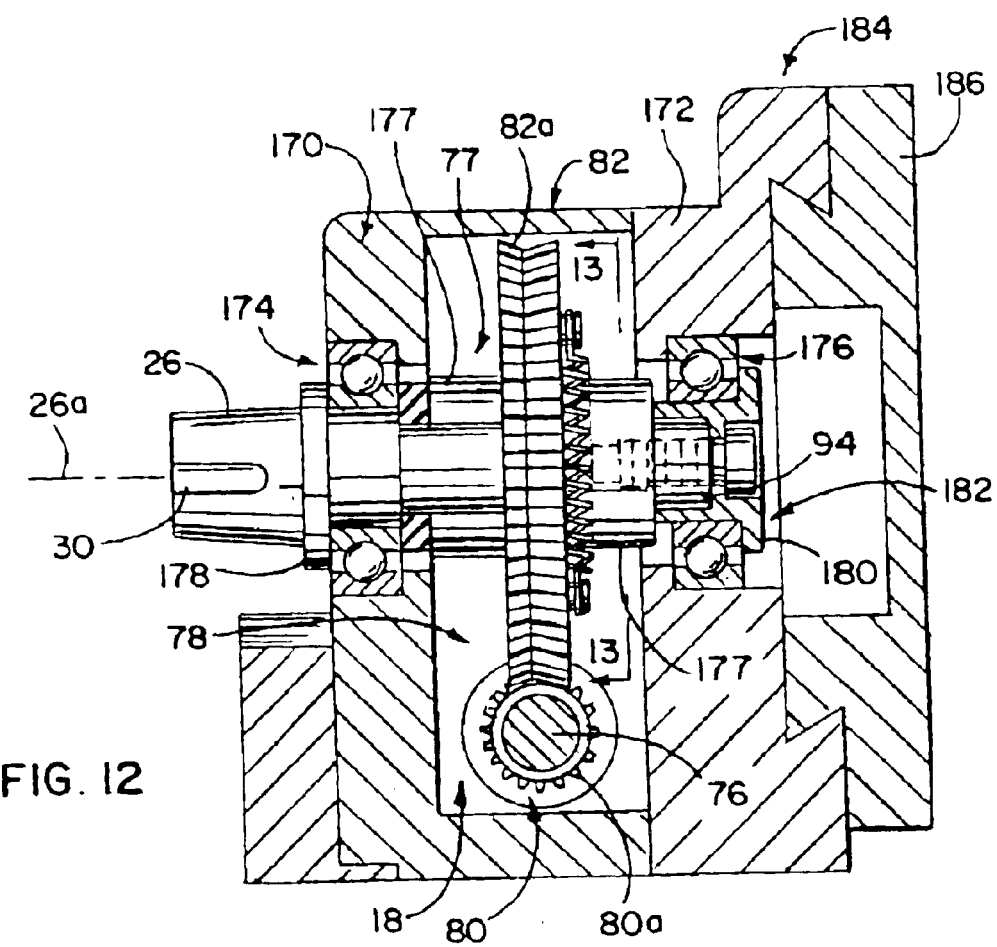
FIG. 12 is a cross-sectional view taken along lines 12—12 of FIG. 10 showing a pinion gear on the motor drive shaft meshed with the anti-backlash gear including a biased split gear on the output shaft assembly.
Figure 13:
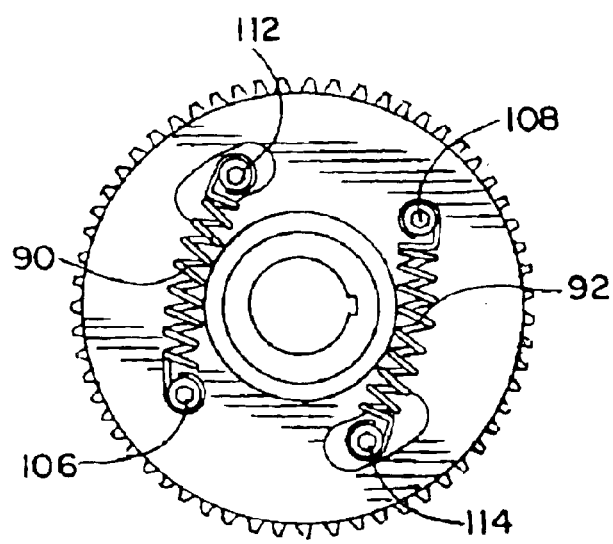
FIG. 13 is an elevational view of the gear assembly of the gear assembly taken along line 13—13 of FIG. 12 showing the biasing mechanism for urging the split gears angularly opposite to one another.
Figure 14:
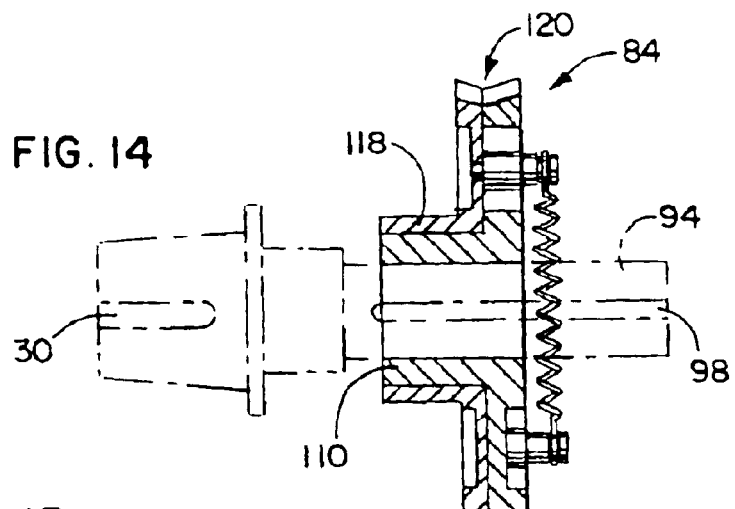
FIG. 14 is a cross-sectional view of the split gears assembled and biased relative to each other via springs attached between respective posts of each of the split gear members.
Figure 15:
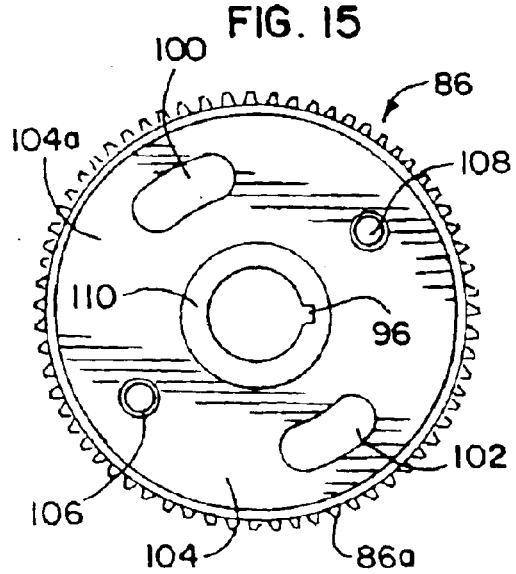
FIG. 15 is a front-elevational view of one of the split gear members showing slots and posts on one of the faces thereof.

To minimize measurement inaccuracies caused by backlash, the above-described worm gearing 78 is provided with an anti-backlash mechanism 84, as can be seen in FIGS. 10–19. More particularly, the worm wheel 82 is split axially so that there are two annular gear portions 86 and 88 which are angularly or rotatably biased relative to each other as by at least one and preferably two springs 90 and 92 such that the gear teeth 82a stay in positive contact with the gear teeth 80a at substantially all times even when the motor 72 reverses, such as when the x-ray head reaches an end of its arcuate path 22 during a measurement operation. As shown in FIG. 14, the gear portion 86 is keyed to main shaft portion 94 of the output shaft assembly 77 so as to be fixed up for rotation therewith as by a key slot 96 formed on the interior diameter of the gear portion 86 and an axial projection 98 formed on the main shaft portion 94 of shaft assembly 77. The gear portion 86 includes arcuate guide slots 100 and 102 (FIG. 15) extending through the annular body 104 thereof. A pair of stand-off bosses or posts 106 and 108 extend axially from surface 104a of the gear body 104. The guide slots 100 and 102 are formed at diametrically opposite positions in the gear body 104 so as to be spaced by approximately 180 degrees from each other. The posts 106 and 108 are also diametrically oppositely positioned to each other spaced by 180 degrees around the gear body 104 and by approximately 90 degrees from each of the slot openings 100 and 102.

Figure 11:
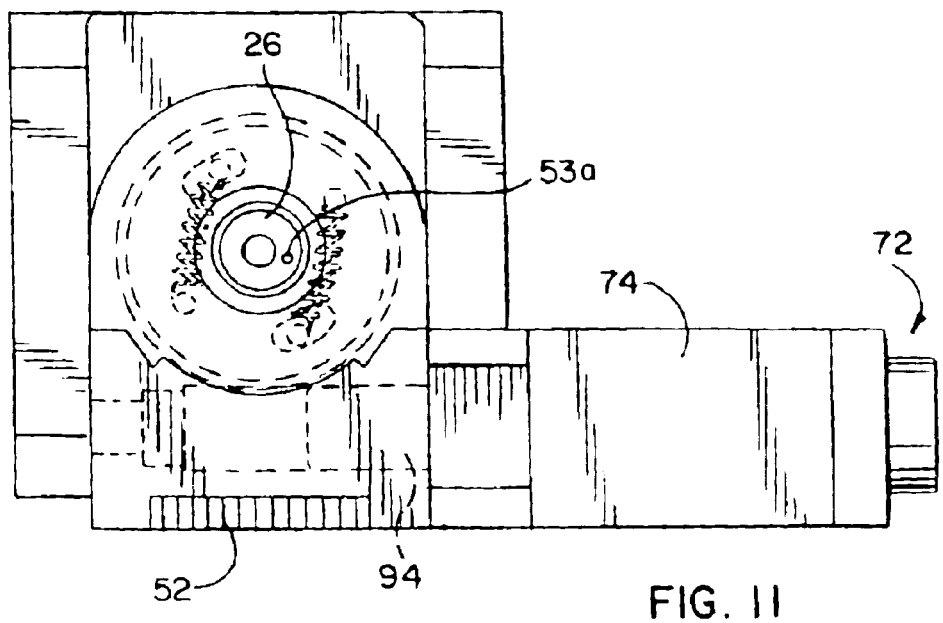
FIG. 11 is a front elevational view of the drive assembly taken along line 11—11 of FIG. 10 and showing in phantom the motor drive shaft and an anti-backlash gear assembly associated with the output shaft.
Figure 16:
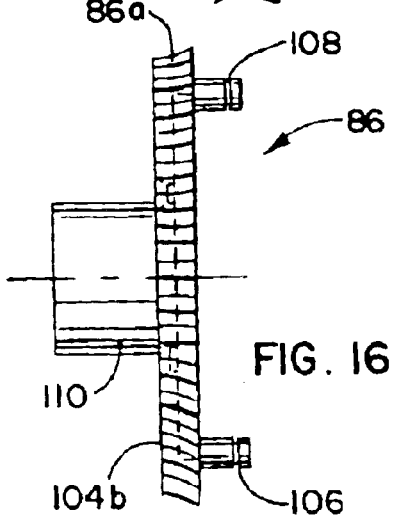
FIG. 16 is a side-elevational view of the split gear member of FIG. 15.
Figure 17:
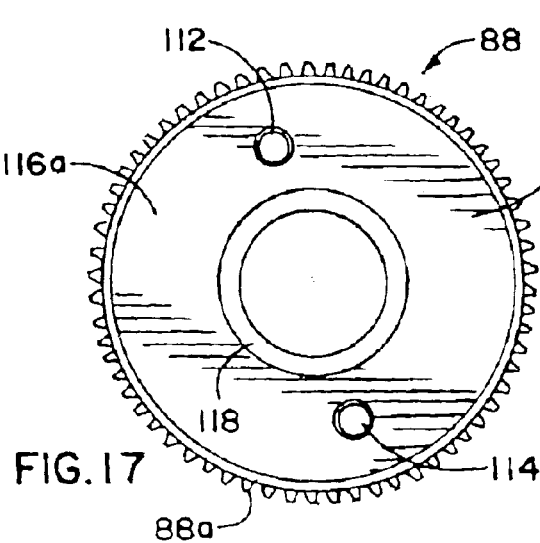
FIG. 17 is a front-elevational view of the other one of the split gear members showing posts on the face thereof.
Figure 18:
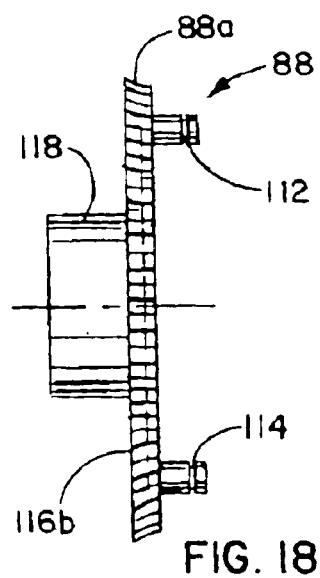
FIG. 18 is a side-elevational view of the split gear member of FIG. 17.

The gear portion 88 is mounted to the shaft portion 94 so as to freely rotate with respect thereto. As shown in FIGS. 14 and 16, the gear portion 86 includes a hub portion 110 that extends axially from surface 104b, and which includes the slot recess 96 formed therein. The gear portion 88 also includes a pair of stand-off bosses or posts 112 and 114 at diametrically opposite positions in the gear body 116 and which extend axially from surface 116a thereof. The gear body 116 also includes a hub portion 118 which extends axially from opposite surface 116b of the gear body 116, as can be seen in FIG. 18. As shown in FIG. 14, the inner diameter of the hub portion 118 is sized to be approximately the same or slightly larger than the outer diameter of the hub portion 110 so that when the gear portions 86 and 88 are assembled, the hub 118 can rotate about the hub 110. Assembled, the biased gear portions 86 and 88 together cooperate to form the anti-backlash mechanism 84 for the drive assembly 18. For assembly of the anti-backlash mechanism 84, the gear portions 86 and 88 are advanced axially relative to each other so that the respective gear body surfaces 104b and 116a are brought into engagement with the posts 112 and 114 aligned for fitting through the guide slots 100 and 102 and the hub 118 sliding over the hub 110. With the posts 112 and 114 projecting through the slot openings 100 and 102, the springs 90 and 92 are then attached so that they each extend between one of the posts 106, 108 of the gear portion 86 and one of the posts 112, 114 of the gear portion 88, as shown in FIGS. 11 and 13.

Figure 19:
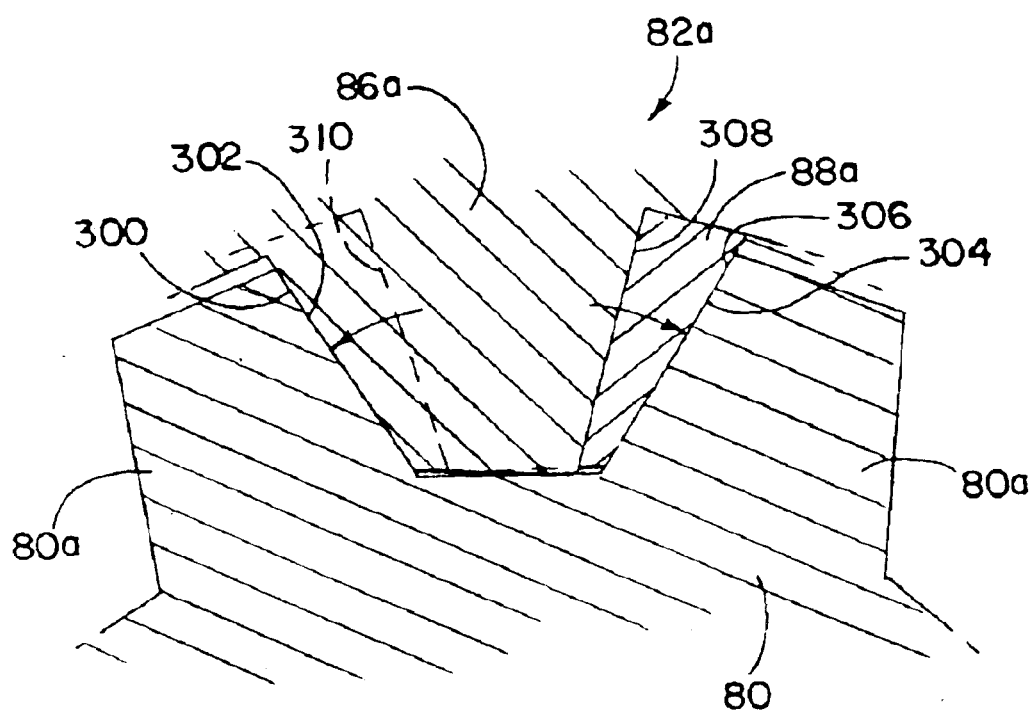
FIG. 19 is a schematic view of the effects of the biasing action on respective gear teeth of the split gear members showing the gear teeth taking up slack between adjacent gear teeth on the pinion gear.

Accordingly, the preferred and illustrated anti-backlash mechanism 84 includes a worm wheel gear 82 that is split axially into two annular gear portions 86 and 88 that are angularly or rotatably preloaded or biased relative to each other so as to maintain positive contact between the gear teeth 82a of the split-gear 82 and the gear teeth 80a of the gear 80, as is shown schematically in FIG. 19. In other words, the biased gear portions 86 and 88 allow the respective drive teeth 86a and 88a formed thereon to stay in engagement with the drive surfaces of the gear teeth 80a at substantially all times during operation of the motor 72 thus avoiding measurement inaccuracies caused by play between intermeshing gear teeth such as found in the prior rack and pinion drive systems that have been previously employed in open beam x-ray diffraction systems. The springs 90 and 92 provides a bias force to the gear teeth 86a and 88a of the split gear 82 disposed between adjacent teeth 80a of the gear 80 so that there is angular displacement therebetween which allows them to stay in constant driving engagement with the gear teeth 80a such that one of the gear tooth portions 86a, 88a is engaged with one tooth 80a during motor operation including during reversals thereof while the other cooperating gear tooth portion 86a, 88a stays in engagement with the next adjacent gear tooth 80a despite sizing of the individual gear tooth portions 86a and 88a to provide clearance between adjacent gear teeth 80a when meshed therebetween.

Referring to FIG. 19, the bias force provided to the split gear 82 causes gear tooth portion 86a and specifically drive surface 300 thereof to stay firmly engaged with the left gear tooth 80a and specifically its facing drive surface 302, and the other cooperating gear tooth portion 88a and specifically drive surface 304 thereof to stay firmly engaged with the right gear tooth 80a and specifically its facing drive surface 306. The surface 308 of gear tooth portion 86a opposite its drive surface 300 is spaced from drive surface 306 of right gear tooth 80a and similarly surface 310 of gear tooth portion 88a opposite its drive surface 304 is spaced from drive surface 302 of left gear tooth 80a. However, the preloaded split-gear 82 is able to take up this gap spacing with one gear tooth portion or the other between adjacent gear teeth of gear 80 to maintain constant driving contact therewith, as described above. Thus, with the anti-backlash mechanism 84 herein, the play that would normally be found between gear teeth is taken up by the biased gear teeth portions 86a and 88a. Accordingly, the preferred drive assembly 18 herein incorporated in the base 14 and provided with the anti-backlash mechanism 84 allows for precise information to be known regarding the position of the head and the collimator 20 thereof relative to the part 16 being measured.

Referring to FIGS. 16 and 18, the gear teeth portions 86a and 88a can be oppositely tapered or contoured in the axial direction so that when assembled they cooperate to form a concave surface 120 for the composite gear teeth 82a formed by the cooperating gear teeth portions 86a and 88a. The concave profile for the gear surface 120 allows it to better conform to the tooth profile of the worm gear 80. In this way, there is greater contact surface between the teeth 80a and 82a of the meshed gears 80 and 82 to optimize the load carrying capacity of the worm gear drive 78.

Figure 21:
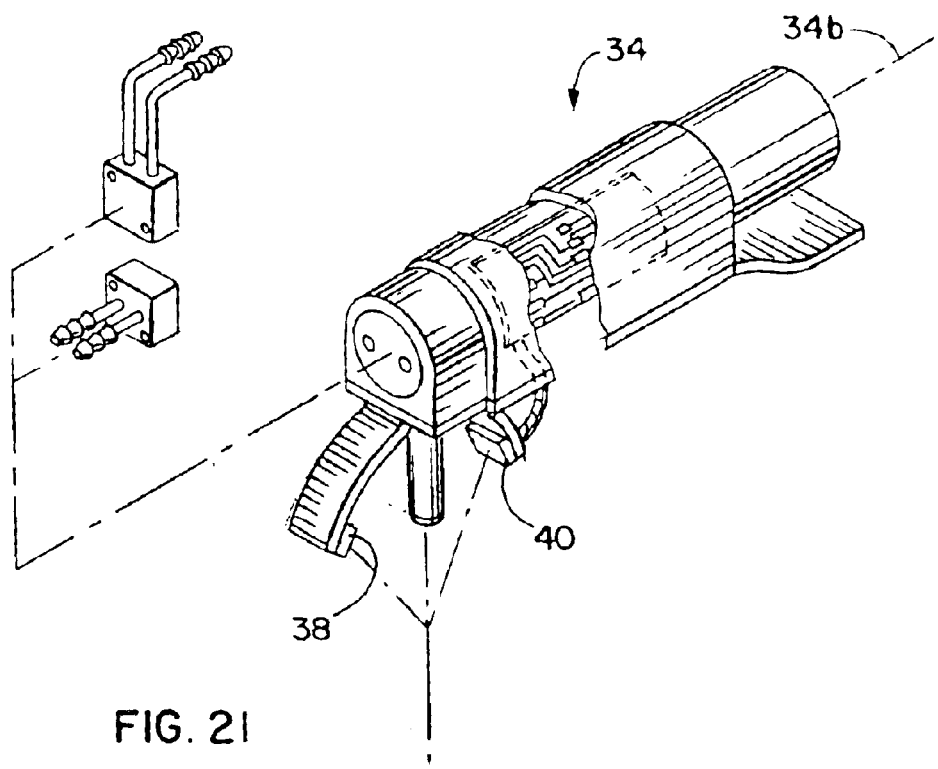
FIG. 21 is a perspective view of the micro-x-ray head showing alternative water manifolds therefor and having the sensors fixed in the d v. $Sine^2\chi$ orientation.
Figure 22:
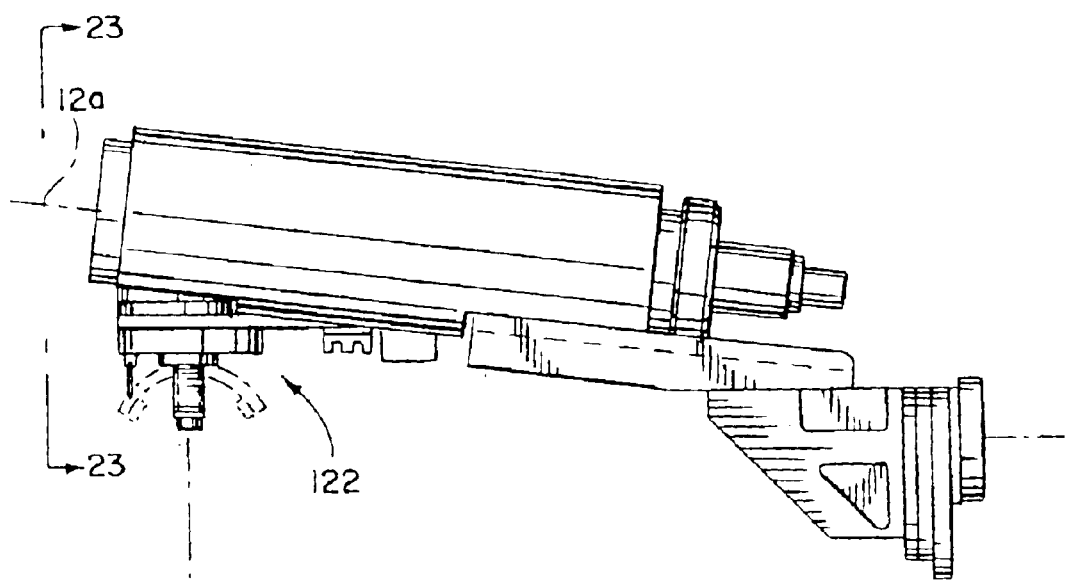
FIG. 22 is a side-elevational view of the large tube x-ray head including a detector shift assembly and showing the sensors in the d v. $Sine^2\psi$ orientation in solid lines and in the d v. $Sine^2\chi$ orientation in phantom lines.

The micro tube 34 can have its detectors 38 and 40 fixed either as shown in FIG. 6 on either side of tube axis 34b or alternately so that they are aligned along the tube axis 34a to improve the maneuverability of the tube 34 in confined spaces, as seen in FIG. 21. Manifestly, the other x-ray heads 12 and 32 can also have two versions so that both measurement techniques can be employed with a particular x-ray tube head size. As mentioned, with the sensors 38 and 40 axially aligned, the measurement technique that is employed i.e. d v. $Sine^2\chi$, reduces measurement accuracy.

Figure 23:
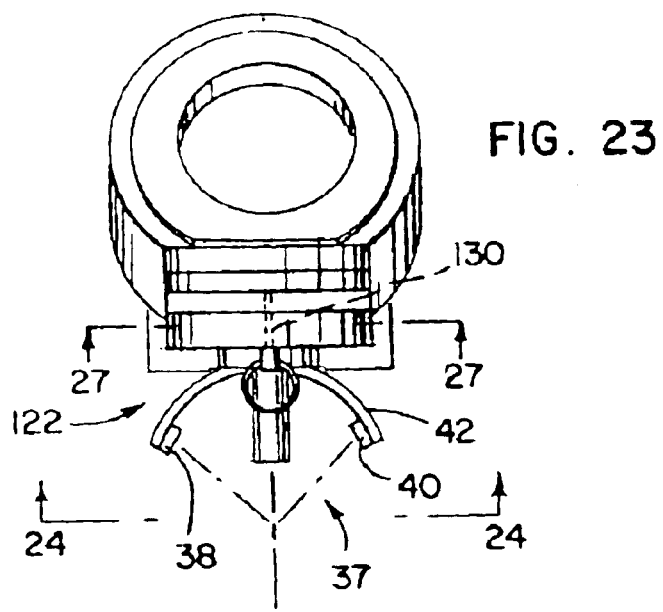
FIG. 23 is a front elevational view of the head and detector shift assembly of FIG. 22 showing a manual pull ring actuator for releasably securing a rotary shift member to a mount member thereof.
Figure 24:
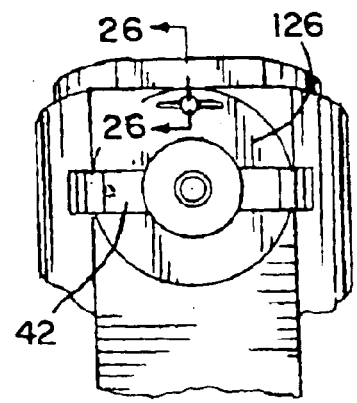
FIG. 24 is a fragmentary bottom plan view of the head and detector shift assembly of FIGS. 22 and 23.
Figure 25:
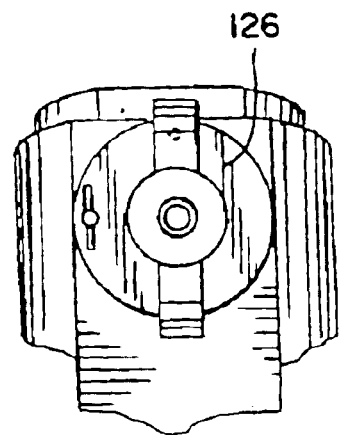
FIG. 25 is a bottom plan view similar to FIG. 24 showing the detectors shifted to their d v. $Sine^2\chi$ orientation aligned with the x-ray tube axis.

Referring now to FIGS. 22–26, a detector adjuster or shift assembly 122 is shown which allows a user to shift the fiberoptic detectors 38 and 40 between either of the two positions corresponding to the measurement technique desired to be employed, i.e. d v. $Sine^2\psi$ or d v. $Sine^2\chi$. The detector adjustment assembly 122 provides significant flexibility by allowing for either measurement technique to be utilized depending on the needs of the measurement operation to be undertaken without the need for changing x-ray heads or utilizing a different x-ray diffraction unit as previously required. Thus, if accuracy is not as critical and accessibility to difficult to access spaces is more important, the detector adjustment assembly 122 can be employed to shift the detectors 38 and 40 so that they are aligned along the tube axis 12a, as shown in FIG. 25 with the d v. $Sine^2\chi$ measurement technique employed. On the other hand, where accuracy is more important than maneuverability of the x-ray head, the detectors 38 and 40 can be shifted to their position where they are spaced laterally on either side of tube axis, as shown in FIGS. 23 and 24 rotated substantially 90 degrees from the position of FIG. 25 for implementing the d v. $Sine^2\psi$ measurement technique.

Accordingly, the detector adjust assembly 122 obviates the need to provide a different x-ray head for each of the two measurement techniques. Although the assembly could be implemented with the microhead 34, it has been found that to obtain the maximum benefits of the reduced size of the head 34, it is preferred to provide two versions thereof as shown in FIGS. 6 and 21 with the detector arc mount 41 fixed or integrally formed with the tube housing 54.

The detector adjustment assembly 122 can include a manual actuator such as in the form of a pull ring assembly 124 that allows an operator to manually adjust the position of the detector assembly 37. More specifically, the assembly 122 includes a shift member in the form of a rotary disk 126 having the detector mount 42 fixed thereto. The rotary disk 126 can be secured in a selected one of two different positions relative to disk mount member 128 thereabove with the two positions corresponding to the two x-ray diffraction measurement techniques discussed herein. To this end, the disk mount member 128 includes a pair of apertures 130 and 132 that are spaced 90 degrees from each other to correspond to the d v. $Sine^2\psi$ and d v. $Sine^2\chi$ measurement techniques, respectively.

Figure 26:
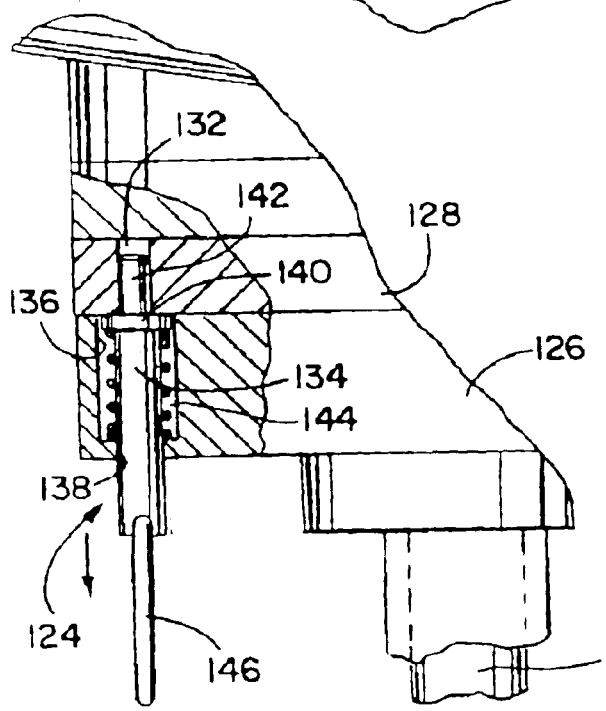
FIG. 26 is an enlarged side elevational view partially in section as taken along line 26—26 of FIG. 24 showing a spring loaded plunger member of the pull ring actuator received in aligned openings in the shift and mount members.

The rotary disk member 126 carries a plunger member 134 of the pull ring assembly 124. The plunger member 134 is spring loaded in through bore 136 formed in the disk member 126. The through bore 136 can be aligned with either one of the apertures 130 and 132 to fix the position of the detector system 37 as desired. Referring to FIG. 26, the through bore 136 has a radially extending lip wall portion 138 extending about the bottom opening thereto. The plunger member 134 has a radially enlarged collar portion 140 having a diameter that is larger than that of the apertures 130 and 132 in the disk mount member 128. Extending upwardly from the plunger collar portion 140 is an upper pin portion 142 of the plunger member 134 sized to fit into the apertures 130 and 132. Spring 144 biases the pin portion 142 in an upward direction and into one of the apertures 130 and 132 when aligned therewith. The spring 144 can include coils extending about the plunger member 134 with the end coils seated against the wall portion 138 and the collar portion 140. The plunger member 134 extends downwardly out through the opening formed by the wall portion 138 and has a pull ring 146 secured at the lower end thereof.

Figure 27:
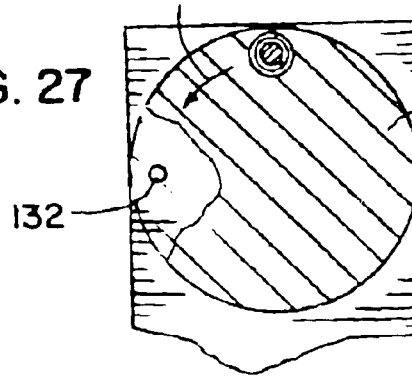
FIG. 27 is a bottom plan view partially in section as taken along line 27—27 of FIG. 23 showing another opening in the mount member for receiving the plunger with the detectors shifted to the d v. $Sine^2\chi$ orientation.

As shown in FIGS. 23, 24 and 27, the pin portion 142 is biased into the aperture 130 such that the detectors 38 and 40 are disposed on either side of the tube axis and the d v. $Sine^2\psi$ measurement technique is employed for x-ray diffraction measurement operations. To switch the configuration of the detector system 37, an operator pulls downward on the plunger member 134 via the pull ring 146 so that the pin portion 142 is retracted out from the aperture 130 against the bias force provided by the spring 144 with the spring coils compressed between the wall portion 138 and plunger collar portion 140. The operator then rotates the disk member 126 in rotary direction 148 as indicated by the arrow in FIG. 27 until the plunger member 134 is aligned with the aperture 132. At this point, the operator releases the pull ring 146 and the bias force provided by spring 144 urges the pin portion 142 into the aperture 132 of the mount member 128 to fix the position of the detector system in the d v. $Sine^2\chi$ orientation with the detectors 38 and 40 aligned along the tube axis of the x-ray head.

Turning to more of the details, each of the x-ray heads 12, 32 and 34 are mounted to a carrier support 150 that extends rearwardly from the x-ray head housing to depending flange mount portion 152 at the rear end thereof. The rear flange mount portion 152 includes the socket adapter portion 28 which is configured identically for each head and carrier support 150 thereof including for head 200 and its previously-described carrier support 206. Each carrier support 150 includes a forwardly extending cantilevered support portion 154 which carries the heads 12, 32 and 34 thereon such that their respective longitudinal axes 12b, 32b and 34b extend generally in the fore and aft x-axis direction offset from the socket axis 28a and spaced thereabove. In this manner, operation of the common drive assembly 18 causes the heads 12, 32 and 34 and their collimators 20 to traverse or sweep through the arcuate path 22 which is centered on the offset axis 28a of the socket adapter 28 of each of the heads. Similarly, the socket axis 28a will generally be offset from the tube 200a of head assembly 200 so that operation of the drive assembly 18 causes its collimator 20 to traverse arcuate path 22. Together, the shaft adapter portion 26 and the socket adapter portion 28 cooperate to align each head in the same predetermined position each time one is connected to the base unit 14. Accordingly, with the any of the heads 12, 32, 34, and 200 detachably connected to the base unit 14, the shaft adapter axis 26a will be aligned with the socket axis 28a to provide consistent and repeatable positioning of the modular x-ray heads herein.

Continuing reference to FIGS. 3–5, the carrier support 150 for the smaller heads 32 and 34 can be substantially identical in terms of the forward cantilevered portion 154 thereof, whereas the support 150 for the large x-ray head 12 can be modified to provide the heavier head 12 with more robust support. As illustrated in FIGS. 1–3, the forward extension portion 154 can have a cradle configuration including arcuate side portions 156 and 158 that extend up from the bottom around either side of the rear portion of the large x-ray head 12 to provide a cradling thereof with underneath and side support for the head 12. Further reinforcement can be provided by gussetting 160 provided between the rear end portion of the carrier support 150 and the depending flange portion 152, as best seen in FIG. 3. By contrast, the smaller size and lighter weight of the heads 32 and 34 substantially obviates the need for the robust construction for the carrier supports 150 thereof. As shown, the intermediate size head 32 is carried out on front end portion 162 of the carrier portion 154. The extreme light weight of the microhead 34 allows it to be secured in line with the carrier portion 154 so that its rear end 164 is secured in substantial face-to-face relation to the front end 166 of the carrier support 150, as shown in FIG. 5. The aligned mounting of the microhead 34 also improves its maneuverability as the forward support portion 154 is substantially the same diameter as that of the microhead's tubular housing 54.

Figure 10:
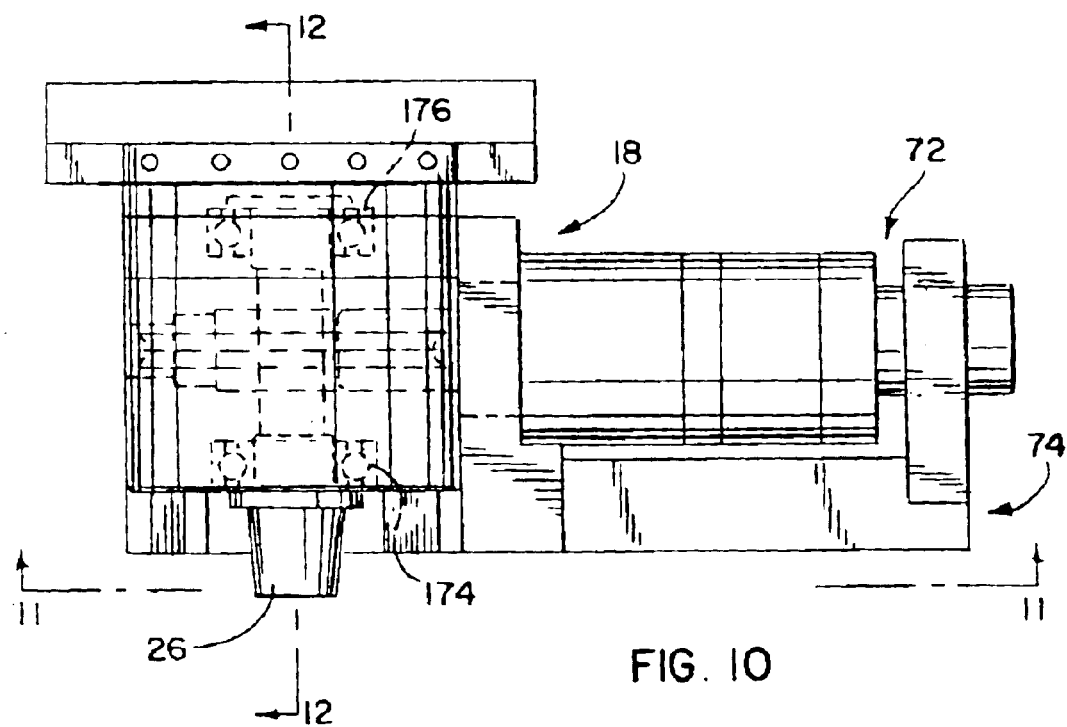
FIG. 10 is a plan view taken along line 10—10 of FIG. 1 of the drive assembly showing the motor and the frusto-conical configuration of the output adaptor shaft end portion.

Referring next to FIGS. 2, 10 and 12, it can be seen that the worm gear drive 78 is housed in an annular casing 168. The casing 168 includes front and rear wall portions 170 and 172 that are counterbored for receipt of high precision bearings such as ball bearings 174 and 176, respectively, therein. The shaft assembly 77 is journalled for rotation by the bearings 174 and 176 with the conical adapter portion 26 projecting forwardly from the front wall portion 170. Bushings 177 can also be provided about the shaft assembly 77, and in particular the main shaft portion 94 for provided bearing support thereto. Radially enlarged front and rear flanges 178 and 180 cooperate to capture the shaft assembly 77 tightly against and for rotation with the respective bearings 174 and 176. As shown in FIG. 12, the rear flange 180 can be formed on a rear cap member 182 that is bolted to the rear end of the main shaft 94 for output shaft assembly purposes. The motor casing 168 can be secured to or integrally formed with a y-axis carrier 184 at the rear thereof that is mounted as by a dovetail fit to a z-axis carrier 186 which can slide vertically up and down along vertical stand 188 of the base unit frame 19.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A modular x-ray diffraction system for taking x-ray diffraction measurements from different parts, the x-ray diffraction system comprising:

a base;

a plurality of modular x-ray heads for being detachably connected to the base, each of the heads including an x-ray emitter;

a common drive assembly associated with the base for shifting the head connected to the base in an arcuate path during an x-ray diffraction measurement operation; and an adapter between the base and the x-ray heads for connecting and detaching the heads from the base to allow an operator to select the head to be used for a particular x-ray diffraction measurement operation.

2. The modular x-ray diffraction system of claim 1 wherein the adapter includes portions associated with the base and each of the heads with the portions having a predetermined mating configuration so the base and head adapter portions are removably received one within the other.

3. The modular x-ray diffraction system of claim 1 wherein the adapter comprises an output shaft portion of the drive assembly and an identical socket associated with each of the heads and configured to receive the shaft portion therein.

4. The modular x-ray diffraction system of claim 1 wherein the heads include different predetermined operational characteristics from each other to allow the head to be selected for being connected to the base that optimize measurement performance for a particular measurement operation to be undertaken.

5. The modular x-ray diffraction system of claim 4 wherein the operational characteristics comprise x-ray head power, x-ray wavelength, and x-ray beam shape.

6. The modular x-ray diffraction system of claim 4 wherein the heads each include a control module, the base has a controller associated therewith, and
a link for interconnecting the module to the controller for transmission of the head's predetermined operational characteristics to the controller.

7. The modular x-ray diffraction system of claim 1 wherein the plurality of x-ray heads include heads of different sizes to allow smaller heads to be employed where access to confined spaces is desired.

8. The modular x-ray diffraction system of claim 1 wherein the drive assembly includes gearing having an anti-backlash mechanism for precision shifting of the heads in the arcuate path during x-ray diffraction measurement operations.

9. The modular x-ray diffraction system of claim 1 wherein the drive assembly includes a motor, a drive shaft driven by motor operation, and an output shaft, and the adapter comprises an adapter end portion of the output shaft and an adapter socket opening associated with each of the heads for receiving the shaft end portion therein, and
a drive shaft gear and an output shaft gear that cooperate to transmit power from the drive shaft to the output shaft for shifting of the connected head in the arcuate path via the adapter with one of the gears being split and including gear portions that are rotatively biased relative to each other to minimize play between teeth of the drive shaft and output shaft gears.

10. The modular x-ray diffraction system of claim 1 wherein the plurality of modular x-ray heads include a microhead including a tubular housing of approximately 1.25 inches or less for fitting in confined spaces.

11. A modular x-ray diffraction system for taking x-ray diffraction measurements from different parts, the x-ray diffraction system comprising:
a base;
a plurality of modular x-ray heads for being detachably connected to the base:
a common drive assembly associated with the base for shifting the head connected to the base in an arcuate path during an x-ray diffraction measurement operation: and
an adapter between the base and the x-ray heads for connecting and detaching the heads from the base to allow an operator to select the head to be used for a particular x-ray diffraction measurement operation,
wherein the heads include x-ray detectors and an x-ray emitter, and
a detector adjustment assembly for shifting the detectors between at least two positions associated with two different x-ray diffraction measurement techniques.

12. A modular x-ray diffraction system for taking x-ray diffraction measurements from different parts, the x-ray diffraction system comprising:
a base;
a plurality of modular x-ray heads for being detachably connected to the base each of the heads including an x-ray emitter;
a common drive assembly associated with the base for shifting the head connected to the base in an arcuate path during an x-ray diffraction measurement operation; and
an adapter between the base and the x-ray heads for connecting and detaching the heads from the base to allow an operator to select the head to be used for a particular x-ray diffraction measurement operation,
wherein the plurality of modular x-ray heads includes a microhead having a housing of minimum size for optimized access to confined spaces, x-ray detectors, and a flexible substrate having circuitry that processes signals from the detectors with the flexible substrate wrapped about the housing to substantially conform thereto to keep the housing size to a minimum.

13. An x-ray diffraction apparatus comprising:
an elongate x-ray head for generating x-rays, the elongate x-ray head having opposite ends and a central longitudinal axis extending therebetween;
an emitter of the head adjacent one of the head ends, for directing x-rays at a part from which x-ray diffractions measurements are to be taken;
detectors carried by the elongate head adjacent the one head end and the emitter, with the detectors detecting the diffracted x-rays; and
a detector adjust assembly including a shift member to which the detectors are mounted and an actuator for allowing the detectors to be shifted from one position to another position relative to the head for employing different x-ray diffraction measurement techniques with the x-ray head.

14. The x-ray diffraction apparatus of claim 13 wherein the shift member is a rotary shift member for being rotated between the different positions.

15. The x-ray diffraction apparatus of claim 13 wherein the actuator of the detector adjustment assembly is a manual actuator.

16. The x-ray diffraction apparatus of claim 15 wherein the manual actuator comprises a spring loaded plunger, and apertures at different positions each one corresponding to one of the different positions for the detectors with the plunger being biased into the apertures when aligned therewith.

17. An x-ray diffraction apparatus comprising:
an elongate x-ray head for generating x-rays;
an emitter of the head for directing x-rays at a part from which x-ray diffractions measurements are to be taken;
detectors of the head that detect the diffracted x-rays; and
a detector adjust assembly including a shift member to which the detectors are mounted and an actuator for allowing the detectors to be shifted from one position to another position relative to the head for employing different x-ray diffraction measurement techniques with the x-ray head,
wherein the x-ray head includes a longitudinal axis and the detector adjustment assembly allow the detectors to be shifted between two positions with the detectors spaced laterally on either side of the x-ray head axis in one position and aligned along the axis in the other position.

* * * * *

UNITED STATES PATENT AND TRADEMARK OFFICE
CERTIFICATE OF CORRECTION

PATENT NO. : 6,925,146 B2
DATED : August 2, 2005
INVENTOR(S) : Brauss

It is certified that error appears in the above-identified patent and that said Letters Patent is hereby corrected as shown below:

Title page,
Item [73], Assignee, after "Oldcastle" insert -- Canada --.

Column 17,
Line 62, after "base" insert -- , -- (comma);

Column 18,
Line 36, change "adjustment" to -- adjust --;
Line 47, change "diffractions" to -- diffraction --;
Line 56, change "adjustment" to -- adjust --; and
Line 56, change "allow" to -- allows --.

Signed and Sealed this

Eighth Day of November, 2005

JON W. DUDAS
*Director of the United States Patent and Trademark Office*